United States Patent [19]
Zarow

[11] 4,219,619
[45] Aug. 26, 1980

[54] VIBRATING DENTAL INSTRUMENT FOR SETTING CROWNS

[76] Inventor: Merle C. Zarow, 13904 Fiji Way #342, Marina del Rey, Calif. 90291

[21] Appl. No.: 940,844

[22] Filed: Sep. 8, 1978

Related U.S. Application Data

[63] Continuation-in-part of Ser. No. 798,561, May 16, 1977, abandoned.

[51] Int. Cl.² .................... A61C 1/07; A61C 3/03
[52] U.S. Cl. ............................ 433/118; 433/218; 128/62 A
[58] Field of Search ............... 32/14 R, 40 R, 40 A, 32/41, 42, 53, 54, 55, 56, 58; 128/12, 62 A; 433/118, 218, 219

[56] References Cited

U.S. PATENT DOCUMENTS

| | | | |
|---|---|---|---|
| 1,694,636 | 12/1928 | Barker | 128/62 A X |
| 2,134,934 | 11/1938 | Wilhoit | 128/62 A X |
| 3,115,139 | 12/1963 | Schneider | 128/62 A |
| 3,267,623 | 8/1966 | Block | 32/58 X |
| 3,293,748 | 12/1966 | Skinner | 128/62 A X |
| 3,466,689 | 9/1969 | Aurelio et al. | 128/62 A |
| 3,526,962 | 9/1970 | Fuerst | 128/62 A X |
| 3,651,576 | 3/1972 | Massa | 128/62 A X |

FOREIGN PATENT DOCUMENTS 1947155  4/1971  Fed. Rep. of Germany ........ 128/62 A Primary Examiner—Russell R. Kinsey
Assistant Examiner—Robert P. Swiatek
Attorney, Agent, or Firm—Ralph B. Pastoriza

[57] ABSTRACT

A vibrator utilizing a disposable bite probe subject to vibrations of the vibrator is used to seat crowns, bridges and the like. After cement has been applied to the underside of the crown and the prepared tooth surface and the crown initially positioned, the bite probe is received between the crown and opposing teeth in the patient's mouth or dentist's finger in the absence of opposing teeth, the patient or dentist applying pressure on the bite probe. When the vibrator is energized, the vibrations express excess cement working the crown down into a proper and secure position on the patient's tooth. Continued pressure on the bite probe by the patient and/or dentist holds the bite probe in position, the vibrator itself being disconnected from the probe and the probe itself being retained in a stationary position for a sufficient length of time to assure proper seating of the crown as the cement hardens.

5 Claims, 12 Drawing Figures

VIBRATING DENTAL INSTRUMENT FOR SETTING CROWNS

This application is a continuation-in-part of my co-pending application Ser. No. 798,561 filed May 16, 1977, now abandoned, and entitled VIBRATING DENTAL INSTRUMENT FOR SETTING CROWNS.

This invention relates generally to dentistry and more particularly to a novel instrument for use by a dentist in removal of cement, during seating of crowns, dental bridges and the like.

BACKGROUND OF THE INVENTION

In the cementing of crowns, dental bridges, restorations and the like on patient's teeth, a relatively thick but flowable cement is utilized, the overlying engaging surface of the crown being provided with such cement and the prepared surface of the tooth similarly provided. The dentist will then position the crown over the prepared tooth and generally work the same into proper position by lateral rocking together with simple manual manipulation of the crown. Because the cement sets fairly rapidly it is important that the dentist operate quickly. Problems are often encountered in that air bubbles are trapped under the crown. Further, there is a substantial hydrostatic back pressure created by the thickness of the cement necessitating extremely rapid attempts to fully seat the crown. Before the cement hardens excess cement tends to ooze out of marginal areas, creating cement margins. Moreover, if the applied pressure in setting the crown is not fairly evenly distributed, the crown itself may seat in a canted or slightly tilted position.

BRIEF DESCRIPTION OF THE PRESENT INVENTION

With the foregoing in mind, the present invention contemplates the provision of a crown seating instrument in the form of a vibrator provided with a bite probe receivable between the positioned crown immediately after cement has been applied and the patient's opposing teeth or dentist's finger so that the patient or dentist can apply pressure during vibration. This pressure seats the crown or restorations while the vibration itself breaks down the cement's viscosity and trapped air bubbles. The arrangement permits the excess cement to escape while overcoming the hydrostatic backward pressure created by the thickness of the cement. Moreover, the bite probe is so constructed as to permit deformation and conformation of the opposed areas of the probe to the geometry of the crown and opposing teeth so that proper seating is assured minimizing the risk of any "canting". The relatively rapid vibrations permit seating of the crown very quickly as opposed to former manual pressure techniques with the end in view that the proper seating is achieved before setting-up of the cement itself.

BRIEF DESCRIPTION OF THE DRAWINGS

A better understanding of this invention will be had by now referring to the accompanying drawings in which.

DETAILED DESCRIPTION OF THE INVENTION

Figure 1:
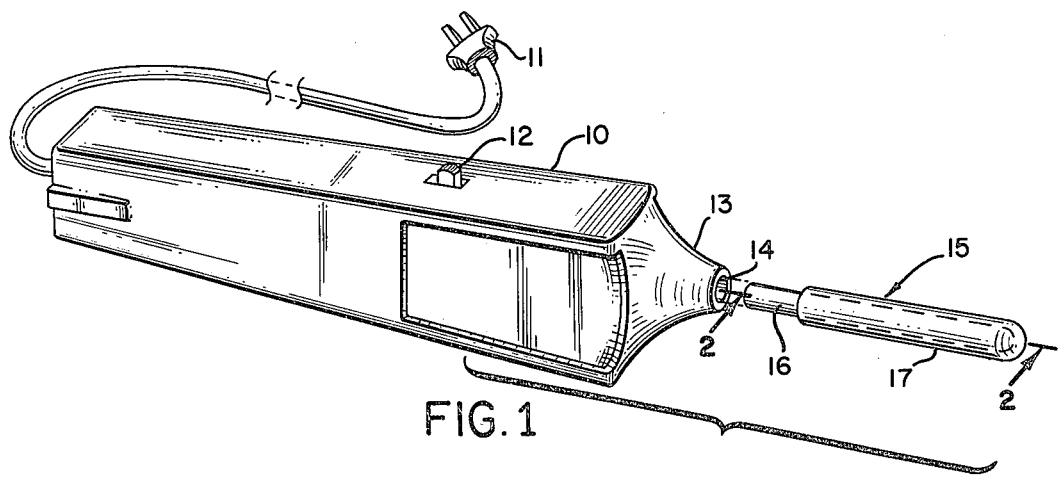
FIG. 1 is a perspective view of a first embodiment of the vibrating dental instrument for setting crowns in accord with the present invention.

Referring first to FIG. 1, a first form of the vibrator is shown at 10. This vibrator incorporates a rechargeable battery and towards this end, there is provided a detachable electrical plug-in wire 11 for recharging the battery from a normal conventional outlet. An on/off manually operable switch 12 is provided as shown.

The forward portion 13 of the vibrator 10 has a nose coupling including means defining a cylindrical bore 14 for receiving a bite probe generally designated by the arrow 15.

Bite probe 15 is a disposable item in the embodiment illustrated and has one end portion 16 removably receivable in the cylindrical bore 14 of the nose coupling and its opposite end portion arranged to be received in a patient's mouth between a patient's teeth after a crown has been positioned thereon and the opposing tooth or teeth in the patient's mouth all as will become clearer as the description proceeds.

Figure 2:
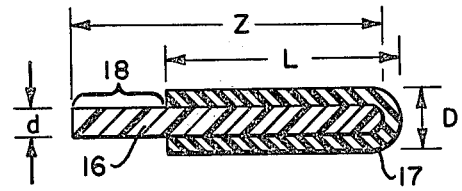
FIG. 2 is a cross section of the bite probe portion of the instrument taken in the direction of the arrows 2—2 of FIG. 1.

In the embodiment shown, the bite probe comprises, as best illustrated in FIG. 2, an elongated core of a first plastic-like material having one end portion comprising the referred to end portion 16 for frictional fit in the nose coupling bore 14 of FIG. 1. A sleeve 17 of a second plastic-like material surrounds the remaining portion of the core as shown in FIG. 2, the sleeve having a length L shorter than the length Z of the core to leave the exposed one end portion 16 as indicated at 18. The outer diameter of the sleeve 17 indicated at D may range from 1.2 to 2.5 times the diameter d of the core 16.

Figure 3:
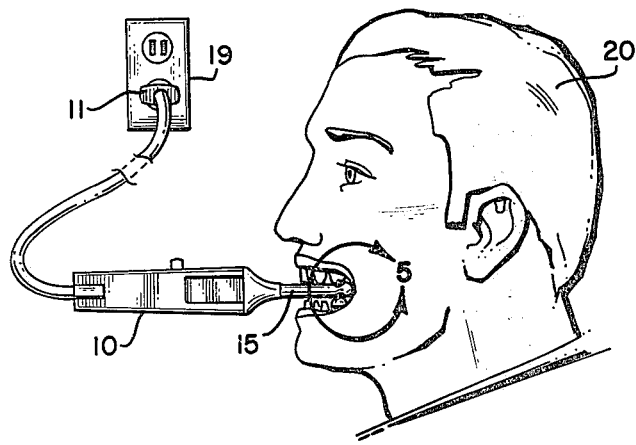
FIG. 3 is a side elevation of the vibrator and bite probe showing the same in use in setting a crown in a patient's mouth.

FIG. 3 illustrates the vibrator 10 with its electrical plug 11 receivable in a conventional socket 19. The other end of the cord is shown disconnected from the vibrator 10 but when it is desired to charge the vibrator 10, this other end of the cord would be received in the base of the vibrator. In FIG. 3, the vibrator 10 would be held by a dentist and positioned in the patient's mouth with the bite probe 15 between the patient's teeth as illustrated.

Figure 4:
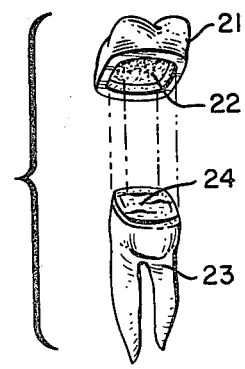
FIG. 4 is an exploded perspective view of a single tooth preparatory to receiving a crown.

Referring to FIG. 4, there is shown a crown 21 wherein the inner overlying surface of the crown has been coated with cement 22. Schematically illustrated below the crown is a patient's tooth 23 having its prepared surface in turn also coated with cement 24.

Figure 5:
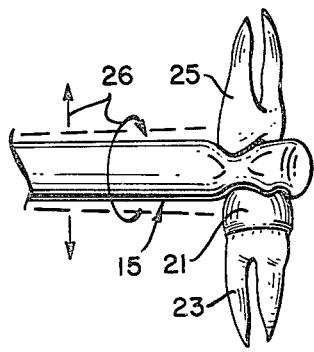
FIG. 5 is an enlarged perspective view of a portion of the bite probe utilized in setting the crown generally encompassed within the circular arrow 5 of FIG. 3.

Referring to FIG. 5, the crown 21 is shown positioned on the tooth 23 with the probe sleeve 15 received between the crown and the patient's opposing tooth 25.

The patient can apply pressure on the bite probe to aid in seating the crown. When the vibrator is energized, the vibrations which generally take place in an up and down and circular direction as indicated by the arrows 26 breaks down the cement's viscosity and trapped air bubbles and rapidly works the crown 21 into its proper seated position on the tooth 23. The rapid vibrations can easily overcome the hydrostatic back pressure created by the thickness of the cement, the rapidity of the seating not permitting sufficient time for the cement itself to set. The result is excellent marginal adaptation together with a reduction in the dangers of cement margins.

After the crown 21 has been seated, the probe sleeve 15 and probe structure remain in the patient's mouth with the patient still applying pressure, the vibrator body 10 itself simply being removed by pulling rearwardly. Because of the simple friction coupling of the one end portion of the probe 16 within the cylindrical bore 14 as described in FIG. 1, the vibrator body 10 can easily be retracted away from the patient's mouth. The patient will retain the bite probe itself between his teeth for a sufficient length of time to assure that the cement has properly hardened. Thereafter, the bite probe is simply disposed of.

Figure 6:
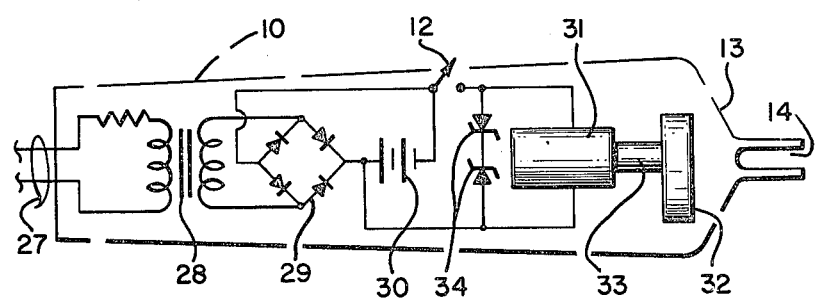
FIG. 6 is a schematic showing of one type of electrical circuit for generating the desired vibrations for the instrument.

FIG. 6 shows a preferred electrical circuit for generating appropriate vibrations. Thus, the vibrator 10 incorporates a rechargeable circuit including appropriate input leads 27 arranged to connect to the cord and plug 11 described in FIGS. 1 and 3. These input leads connect to the primary of a step-down voltage transformer 28, the secondary connecting across opposite vertices of a simple rectifier bridge 29. The remaining vertices in turn connect across a rechargeable battery 30 energizing a direct current electric motor 31. An eccentric weight 32 is secured to the shaft 33 of the motor 31 to thereby generate the desired vibrations when the motor 31 is energized. In the particular embodiment shown, a pair of back-to-back Zener diodes 34 are shown connected across the input leads to the motor 31. These Zener diodes inhibit arcing at the switch 12 from back induction voltage from the motor 31.

The frequency of vibrations will correspond to the speed of the motor. Normally, the frequency of vibration will be in the range of 20-100 vibrations per second.

The outer sleeve 15 of the bite probe described in FIG. 2 is made of softer plastic material than the material used for the core 16; that is, the core 16 is harder than the sleeve. As a result, the sleeve will deform under bite pressure so that the opposite areas of the sleeve in contact with the crown and opposing tooth increase; that is, the surfaces of the sleeve will tend to conform to the geometry of the enlarged portions of the crown and tooth and thus distribute the loading to assure that the crown is driven onto the tooth evenly; that is, without any canting.

Figure 7:
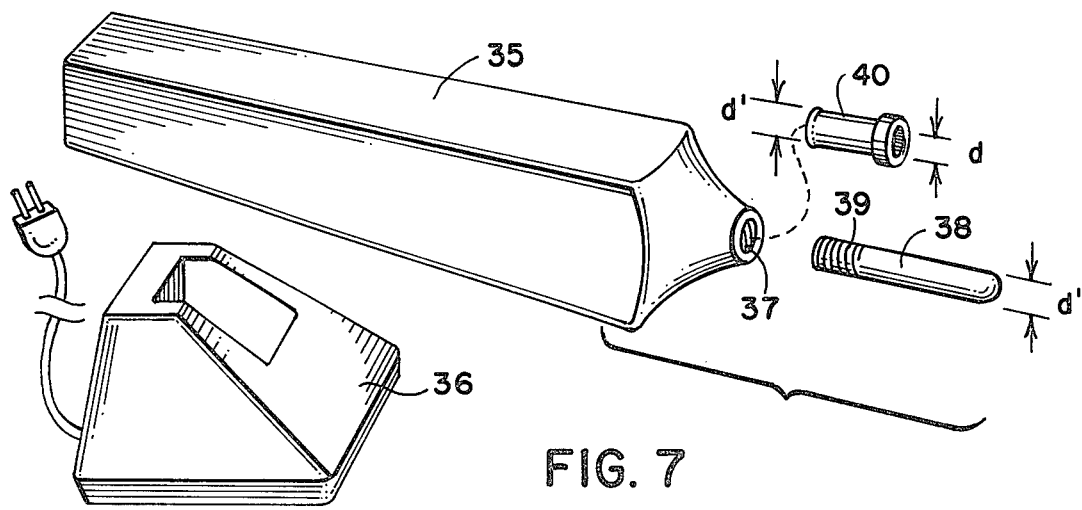
FIG. 7 is a perspective exploded view of a modified embodiment of the vibrating dental instrument utilizing a mandrel for vibrating different bite probes.

Referring now to FIG. 7, there is shown a modified embodiment of the invention in the form of a vibrator 35 differing from the vibrator 10 of FIG. 1 in only two respects. First, rather than have a cord pluggable into the base of the vibrator, there is provided a simple recharging holder 36 having an appropriate opening into which the base of the vibrator 35 can be placed for appropriate recharging of the battery therein. Second, rather than the nose coupling being defined by a bore in the front portion of the vibrator 35, this nose coupling takes the form of a threaded opening 37 for cooperation with the mandrel 38 provided with mating threads 39. The mandrel 38 is of solid metal or plastic and, as will become more evident as the description proceeds, serves to carry a variety of different types of bite probes.

In FIG. 7 there is shown exploded above the mandrel 38 a plastic cap member 40. This cap member is in the form of a cylindrical tube or sleeve which can be inserted in the threaded opening 37. The cap 40 defines a smooth inner bore dimensioned as indicated at d for reception, if desired, of the probe 15 described in FIG. 1. It will be understood, however, that when utilizing the nose coupling in the form of the mandrel, the cap 40 is removed and the mandrel 38 simply threaded in securely to the threaded opening 37 so that the mandrel will vibrate with the forward portion of the vibrator 35 when energized.

Figure 8:
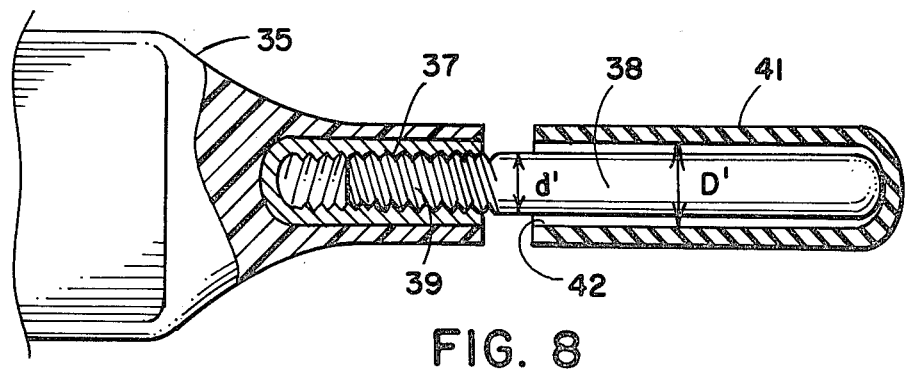
FIG. 8 is an enlarged fragmentary view partly in cross section of the instrument showing the mandrel of FIG. 7 secured in the vibrator with a bite probe positioned thereon.

FIG. 8 illustrates the mandrel 38 fully threaded into the threaded opening 37. Also shown is a tubular end portion 41 of a bite probe receivable over the mandrel 38. It will be noted that the inside diameter D' of the tubular bite probe 41 is greater than the outside diameter d' of the mandrel 38. There thus results an annular clearance between the exterior of the mandrel 38 and the inside cylindrical wall of the tubular portion of the bite probe.

With respect to the foregoing, it is found in certain applications that when the bite probe is "rigidly" secured to the forward portion of the vibrator as described in FIG. 1, biting pressure on the probe by the patient tends in certain instances to dampen the vibrations. With the arrangement described in FIG. 8, the mandrel 38 will be free to vibrate within the clearance area of the probe. Thus, the biting pressure will not tend to dampen the vibrations to the extent that occurs with respect to the bite probe described in FIGS. 1 to 3.

Not only has improved functioning of the vibrator been realizable by the use of the mandrel with the annular clearance relative to the bite probe but by avoiding a friction fit as described, it is very simple to insert and remove the mandrel from the bite probe during the latter part of the seating operation wherein the patient simply holds the bite probe between his teeth for a certain length of time sufficient for complete hardening of the cement after the vibrator has been separated.

In operation, the mandrel 38 is simply inserted into the hollow opening (tube portion) of the bite probe 41 until the extending end of the mandrel just barely touches the inside end of the tubular portion of the bite probe. The bite probe is then positioned as described with respect to the bite probe 15 in FIGS. 3 and 5. However, the material of the tubular portion of the bite probe 41 is of a fairly hard plastic or metal so that it will not deform to the extent that the patient applies pressure directly to the mandrel resulting in the heretofore described undesirable damping. Rather, there may be provided soft pads as a part of the bite probe for proper seating of the bite probe surfaces between the patient's opposing teeth.

Figure 9:
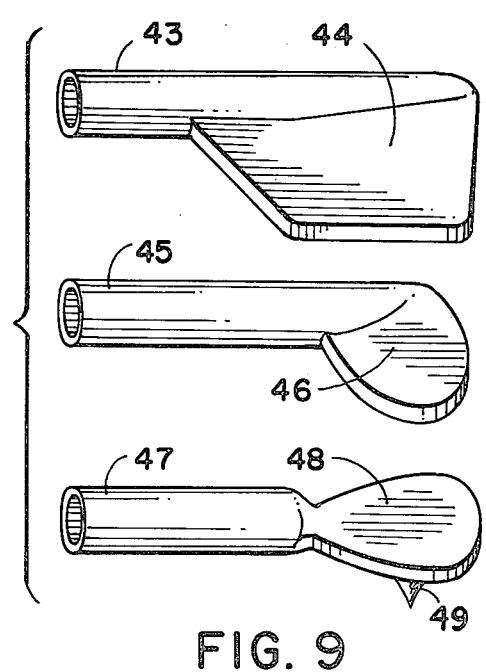
FIG. 9 is a series of three perspective views of different types of bite probes for use with the mandrel and instrument of FIGS. 7 and 8.

FIG. 9 shows a series of different types of bite probes of certain operations depending upon whether a crown is being seated, a bridge, a restoration or the like. Referring specifically to the series of the three bite probes illustrated in FIG. 9, the top view shows a bite probe having one end portion in the form of a tube 43 receivable over the mandrel 38 as described in FIG. 8. The other portion of the bite probe terminates in a shaped portion 44 which is designated with sufficient surface area to engage more than one tooth and restoration (i.e. bridge).

The second bite probe in the series of FIG. 9 is illustrated with a tubular portion 45 and a shaped end portion 46 of a somewhat different configuration from that shown for the first bite probe.

The last bite probe has a tubular portion 47 with yet another shaped portion 48. The shaped portion 48 has a flat top surface and an opposite under surface including a small projection 49, this latter type of bite probe being designed for applying seating vibrations to a specific area.

In all three of the various bite probes described in FIG. 9, the tubular end portions 43, 45 and 47 are identically dimensioned, each having inside diameters corresponding to D' as described in FIG. 8.

Figure 10:
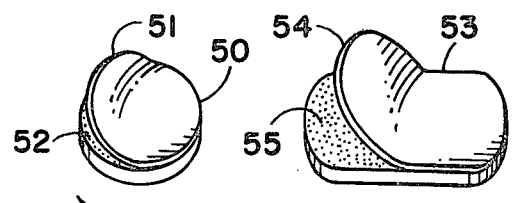
FIG. 10 shows in perspective view two different types of bite probe pads usable with the bite probes of FIG. 9.

FIG. 10 illustrates disposable pads utilized in conjunction with the bite probes of FIG. 9. Merely by way of example, two different types of pads are shown. The first pad is of a circular or disc-shape as indicated at 50. One side of this pad includes a peel-off wax type paper 51 for exposing a self-adhesive surface 52 for securement of the pad to a surface portion of the shaped part of the bite probe.

A second type of pad is illustrated at 53 in FIG. 10 and similarly includes a peelable paper 54 for exposing a self-adhesive surface 55. The shape of the pad 53 in FIG. 10 is designed for use with the bite probe shaped portion 44 of the first bite probe shown in the series in FIG. 9 and would normally be placed on the opposite faces of the shaped portion 44.

Figure 11:
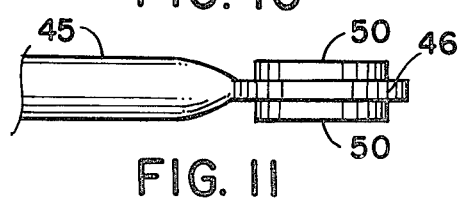
FIG. 11 is a fragmentary side elevation of one of the types of pads of FIG. 10 positioned on the second bite probe in the series of FIG. 9; and, FIG. 12 is a fragmentary side elevation of the manner in which a pad is positioned on the last of the three bite probes shown in FIG. 9.
Figure 12:
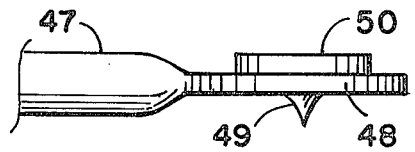

FIG. 11 illustrates by way of example, two of the pads 50 of FIG. 10 in proper position on opposite sides of the shaped portion 46 of the second of the bite probes illustrated in FIG. 9.

Where a concentrated vibrating action is to be achieved in a limited area, a pad 50 might only be used on one surface of the shaped portion of the bite probe. FIG. 12 illustrates such an example for the shaped portion 48 wherein the top surface is provided with a pad 50 while the undersurface is free of such pad so that the projection 49 can be utilized to concentrate the vibrating action.

All of the foregoing is merely illustrative of the fact that many different types of bite probes of different shapes can readily be utilized with the vibrator of this invention. It will be understood with respect to the particular examples of FIGS. 9 through 12, the only disposable portion need be the bite probe pads. The bite probes themselves may be reused after appropriate sterilization.

While the present invention has been described specifically with the setting of a crown on a patient's tooth, it will be understood that the crown involved may be designed to cover several adjacent prepared teeth. Moreover, the vibrator can be used to set dental bridges (fixed partial dentures, inlays, splints, onlays, porcelain to metal crowns and bridges) and similar types of cast restorations. The use of the word "crown" in this specification and in the claims, is merely exemplary and is meant to be synonymous with dental bridges, and similar cast restorations within cement is employed for securing the restoration on a patient's tooth or teeth.

I claim:

1. A vibrating dental instrument for seating crowns wherein the inner, overlying surface of the crown is coated with cement and the prepared exposed surface of the patient's tooth to receive the crown is similarly coated with cement, comprising, in combination:
    (a) a vibrator having a frequency of vibration of from 20–100 vibrations per second and having a nose coupling including a threaded opening subject to vibration when said vibrator is energized;
    (b) a mandrel having a threaded end threadedly receivable in said threaded opening; and
    (c) a removable bite probe having one end portion receivable over said mandrel and its opposite end portion receivable in a patient's mouth between said patient's tooth after said crown has been positioned thereon and the opposing tooth in the patient's mouth, such that the patient can apply pressure by biting on said bite probe, the vibrations imparted to said bite probe upon energization of said vibrator being communicated to said crown to work it into proper position over said tooth, after which said bite probe is retained between the patient's teeth and the vibrator pulled away from said one end portion of the bite probe so that the crown has an opportunity to set with pressure still being applied through said bite probe by the patient.

2. The subject matter of claim 1, in which said nose coupling further includes a cylindrical cap receivable in said threaded opening and defining a smooth cylindrical bore; and an alternate removable bite probe comprising an elongated cylindrical core of a first plastic-like material having one end portion frictionally receivable in said bore; and a sleeve of a second plastic-like material surrounding the remaining portion of said core, the material of said cylindrical core being harder than the material of said sleeve such that bite pressure on said sleeve deforms the opposite areas in contact with the crown and opposing tooth to increase the engagement area whereby the alternate removable bite probe can be optionally used in place of said first mentioned bite probe by insertion of said cap in said threaded opening.

3. The subject matter of claim 1, in which said bite probe has one end portion in the form of an elongated cylindrical tube comprising said one end portion receivable over said mandrel, the inside diameter of said cylindrical tube is greater than the outside diameter of said mandrel to leave a small annular clearance between said mandrel and tube.

4. The subject matter of claim 3, in which said bite probe has a shaped portion spaced from said one end portion for positioning between a patient's teeth; and disposable pad means with self-adhesive backings for affixing to at least one of the surfaces of said shaped portion.

5. The subject matter of claim 1 in which said vibrator incorporates a rechargeable battery; a direct current motor; an eccentric weight mounted to the shaft of said motor; and a manually operable switch for connecting said battery to energize said motor, there being included opposed zener diodes connected across the input leads to said motor to inhibit switch arcing from back generated induction voltage.

* * * * *